United States Patent [19]
Mikhail

[11] Patent Number: 5,284,482
[45] Date of Patent: Feb. 8, 1994

[54] UNIVERSAL PATELLAR CLAMP

[76] Inventor: W. E. Michael Mikhail, 4302 Shamley Green, Toledo, Ohio 43623

[21] Appl. No.: 779,352

[22] Filed: Oct. 18, 1991

Related U.S. Application Data

[63] Continuation-in-part of Ser. No. 652,882, Feb. 8, 1991, Pat. No. 5,180,384.

[51] Int. Cl.$^5$ .............................................. A61F 5/04
[52] U.S. Cl. ........................................ 606/86; 606/88; 606/96; 606/87
[58] Field of Search .................... 606/53, 79, 86, 87, 606/88, 89, 90, 96, 98, 103, 104

[56] References Cited

U.S. PATENT DOCUMENTS

| | | | |
|---|---|---|---|
| 1,985,108 | 12/1934 | Rush | 606/86 |
| 2,181,746 | 11/1939 | Siebrandt | 606/96 |
| 2,291,413 | 7/1942 | Siebrandt | 606/86 |
| 2,427,128 | 9/1947 | Ettinger | 606/86 |
| 2,460,470 | 2/1949 | Rogers | 606/86 |
| 2,583,896 | 1/1952 | Siebrandt | 606/86 |
| 2,631,585 | 3/1953 | Siebrandt | 606/86 |
| 4,364,381 | 12/1982 | Sher et al. | 606/96 |
| 4,633,862 | 1/1987 | Petersen | 606/88 |
| 5,002,547 | 3/1991 | Poggie et al. | 606/96 X |

OTHER PUBLICATIONS

Brochure entitled "Genesis TM Total Knee System Posterior-Stabilized-Surgical Technique", published by Smith+Nephew Richards Inc., 1450 Brooks Road, Memphis, Tenn. 38116.
Brochure entitled "The AMK TM Total Knee System Design Rationale and Surgical Procedure", published by DePuy, Division of Boehringer Mannheim Corporation, Warsaw, Ind. 46580.
Catalog entitled "Whiteside Ortholoc ® Modular Knee System-Total Condylar", Copyright 1989 by Dow Corning Wright, 5677 Airline Road, Arlington, Tenn. 38002.
Brochure entitled "The Intermedics Natural-Knee ® System with Cancellous-Structured Titanium TM", copyright 1987 by Intermedics Orthopedics, Inc. 1300 East Anderson Lane, Austin, Tex. 78752.
Brochure entitled "AGC Total Knee System-Patellar Femoral Systems" published by Biomet ®, Inc., Warsaw, Ind. 46580.
Article entitled "Patellar Prosthesis Positioning in Total Knee Arthroplasty-A Roentgenographic Study" by Luis S. M. Gomes, M.D., Joan E. Bechtold, Ph.D., and Ramon B. Gustilo, M.D., published in the Nov. 1988 issue of Clinical Orthopedics and Related Research, pp. 72-81.
Brochure entitled "Surgical Technique-The Intermedics Natural-Knee ® System", published by Intermedics Orthopedics, 1986.

*Primary Examiner*—Robert A. Hafer
*Assistant Examiner*—Sam Rimell
*Attorney, Agent, or Firm*—Emch, Schaffer, Schaub & Porcello Co.

[57] ABSTRACT

A universal patellar clamp is disclosed. The clamp includes an articular surface clamping member having a central aperture defining a centerline axis. The central aperture is sized to accept all available known sizes of cannulated reamers. An anterior clamping member is positioned along the centerline axis and is movable with respect to the articular clamping member to effect clamping of the patella. A pair of guide arms are engaged with the articular clamping member to be positioned over the central aperture and provide a guide hole for supporting a threaded guidewire or pin along the centerline axis. The guide arms are removable from their position over the central aperture to clear the aperture for access by the cannulated reamer.

13 Claims, 5 Drawing Sheets

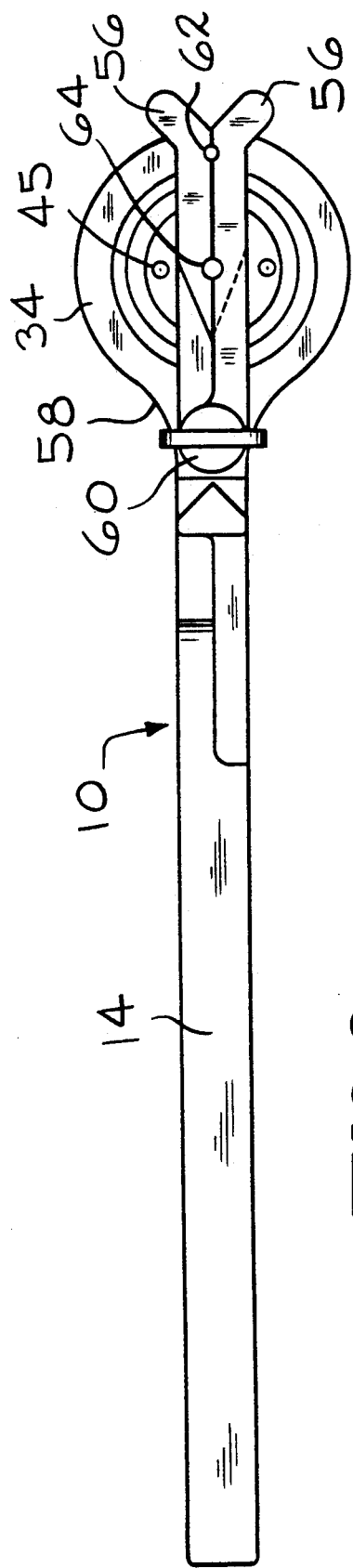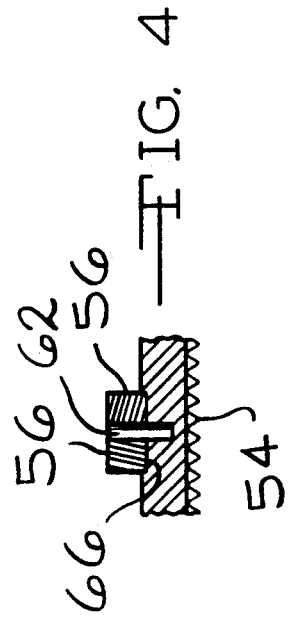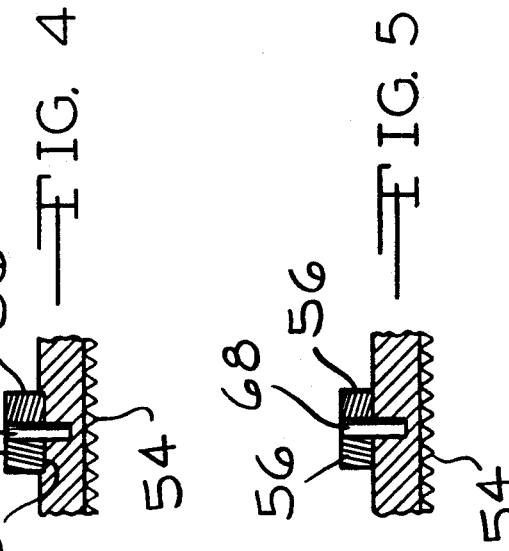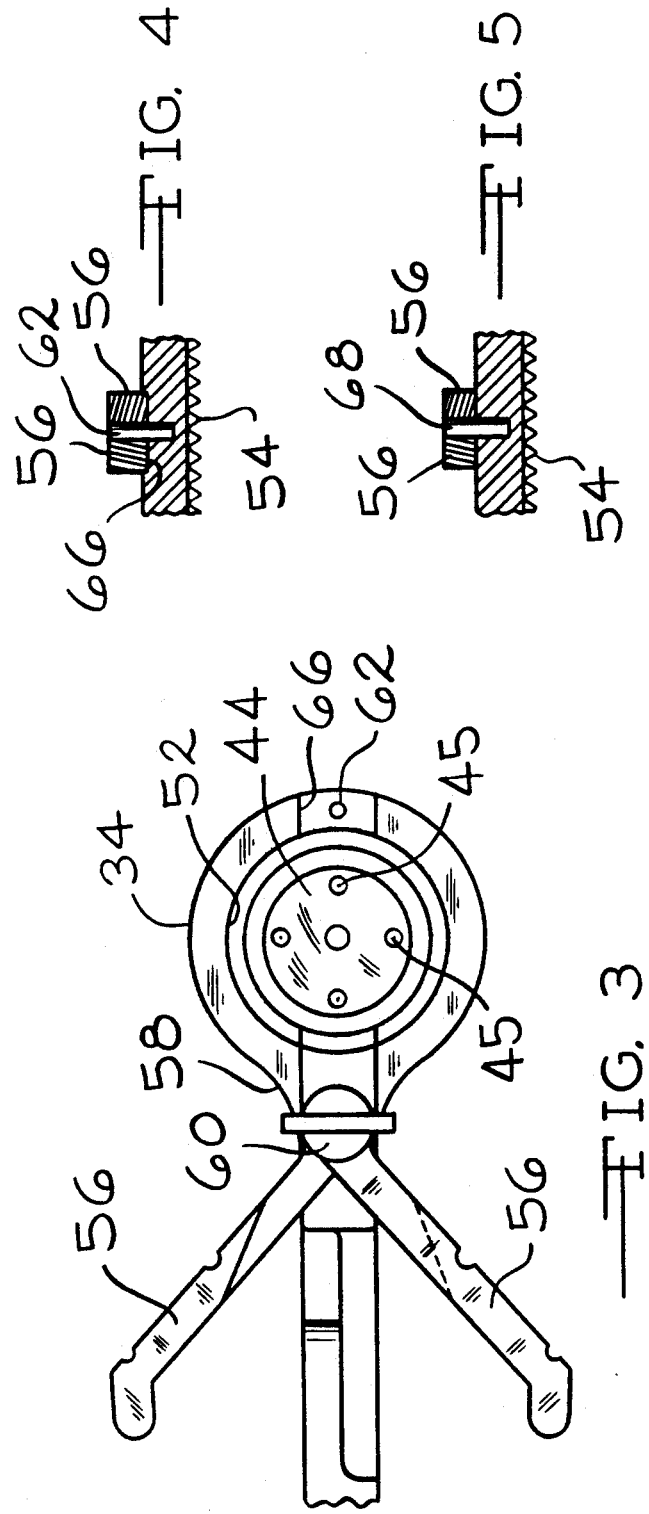

5,284,482

UNIVERSAL PATELLAR CLAMP

This is a continuation-in-part of copending application Ser. No. 07/652,882 filed on Feb. 8, 1991, now U.S. Pat. No. 5,180,384.

BACKGROUND OF THE INVENTION

The present invention is directed to a universal patellar clamp.

In total knee replacement surgery, a prosthesis is provided in which one component is fastened to the distal end of the femur which has been resected and another component is fastened to the proximal end of the tibia which has been resected so that the two components will act together in permitting the leg to bend and straighten out. In performing such surgery, the patella is not normally replaced but rather is resurfaced such that the interior crown portion facing the condyles is cut and reamed to form a cavity in which a patellar prosthesis is implanted. The patellar prosthesis has a crown facing inwardly to engage the patellar or trochlear groove of the femoral component.

In preparing a patella for an implant, it is usually necessary to engage the patella with a clamp having a circular cross sectional configuration and, using the interior surface of the clamp as a guide, ream a cavity in the patella of sufficient size to receive the patellar implant intended to be used. Depending upon a number of factors including the size of the patient, the patellar implant could be one of a number of different sizes. As a result of this, it was, heretofore, necessary to have available a number of clamps each having a different diameter for guiding various size reamers. Typical prior art methods of forming a cavity for implanting a patellar prosthesis are shown and described in the following publications, which are incorporated herein by reference: Brochures entitled "The AMK Total knee System Design Rationale and Surgical Procedure" (page 25), DePuy, Division of Boehringer Mannheim Corporation, Warsaw, Ind., and "WHITESIDE ORTHOLOC® Modular KNEE SYSTEM", copyright 1989 by Dow Corning Wright, Arlington, Tenn. Copies of such references are herewith enclosed.

There has recently been introduced a new design of patellar prosthesis having a tapered surface on the side away from the crown. One such prosthesis is the subject matter of U.S. patent application Ser. No. 07/508,088, filed Oct. 18, 1990, by the applicant herein. The method for implanting such a patellar prosthesis is the subject-matter of my copending U.S. patent application Ser. No. 652,882 and the clamp of my present invention is well-suited for use with the method disclosed in such patent application; however, it should be understood that the apparatus of the present invention is not so limited and may be used with a wide variety of methods for implanting a patellar prosthesis. It has a significant advantage over the prior art for implanting a patellar prosthesis of a type in which one of a number of different sizes is to be used depending upon the patient in that the present invention provides a universally sized patellar clamp to guide the reamer. Accordingly, in utilizing the apparatus of the present invention, it is not necessary to have available a plurality of clamps of varying sizes.

To aid in the understanding of the apparatus of this invention, it is necessary to briefly summarize the surgical method disclosed and claimed in the U.S. patent application Ser. No. 652,882. The '882 invention provides a new method for preparing a human patella for implanting a patellar prosthesis therein and a new method for implanting a patellar prosthesis in a human patella. As is well-known in performing knee replacement surgery, the patella is everted and retained in a position permitting the surgeon to have access to the articular surface which is normally engaged in the intercondylar notch between the condyles. Under the '882 invention, with the patella so supported, the surgeon, using a saw or similar tool for performing osteotomy, removes the top portion of the articular surface, thus leaving a flat surface near the central portion of the patella. Desirably, only a small portion of the articular surface is removed in order to leave as much of the original patella intact as possible. Thus, as pointed out in the above-identified patent application, it is desirable that as little of the human patella be removed as possible.

Following removal of the top of the articular surface a threaded guidewire or pin is used to drill a passageway in the central portion of the patella at substantially right angles to the flat surface. Then, using the threaded guidewire which may be left in the passageway or a rod of similar size to that of the threaded guidewire positioned in said passageway, a cannulated reamer is placed over the threaded guidewire or other guide rod and, using such threaded guidewire or guide rod as a guide, the reamer is utilized to ream the patella thereby forming a cavity having a size and configuration suitable for receiving the patellar prosthesis. Following such reaming, the cavity is cleaned, bone cement placed therein and the patellar prosthesis implanted therein. If desired, the reaming could be performed in stages, initially using a reamer sized to form a relatively small cavity and thereafter using a reamer sized to form the cavity for receiving the patella prosthesis.

DISCLOSURE OF INVENTION

The present invention provides a universal clamp for use in implanting a patellar prosthesis in a human patella. As is well known in performing knee replacement surgery, the patella is everted and retained in a position permitting the surgeon to have access to the articular surface which is normally engaged in the intercondylar notch between the condyles. Under the present invention, a clamp is used to support the patella in a rigid and fixed position so that the patella may be prepared for the patellar prosthesis. The clamp of this invention features a subcutaneous or anterior clamping member placed in opposition to an articular surface clamping member. The subcutaneous or anterior clamping member is positioned to be in conformity with the centerline axis of the articular surface clamping member. The anterior clamping member is movable along the centerline axis of the articular clamping member so that the everted patella may be firmly grasped between the anterior clamping member and the articular clamping member. The articular surface clamping member of this invention is generally donut shaped, defining a central aperture large enough to accommodate the maximum size cannulated reamer needed to ream the patella and form a cavity suitable for receiving the patellar prosthesis. A pair of guide arms, defining a centerline guide hole, are attached to the articular clamping member and rotate about a locking pivot from a position disengaged with the articular clamping member to a position locked in engagement with the articular clamping member, thereby defining a guide hole along the centerline axis of the articular clamping member. The centerline guide hole functions to position the threaded guidewire or pin for drilling a passageway through the central portion of the patella. Once the guidewire is firmly positioned in the passageway, the guide arms can be opened from their engaged positioned with the articular clamping member and the cannulated reamer can be placed in its proper operative position with respect to the patella.

Accordingly, it is an object of the present invention to provide a universal clamp to facilitate the process of implanting a patellar prosthesis in a human patella.

It is a further object of the present invention to provide a clamp having the ability to retain the patella in fixed position and to accept any size cannulated reamer and accurately guide the reamer in its operative function.

It is an additional object of the present invention to provide a universal patellar clamp which utilizes the principles of a cannulated reamer over a guidewire.

Other objects and advantages of the present invention will become apparent from the following detailed description in conjunction with the attached drawings.

BRIEF DESCRIPTION OF THE DRAWINGS

FIG. 2 is a top plan view of the universal patellar clamp of FIG. 1;

FIG. 3 is a fragmentary top plan view of the clamp of FIG. 1 showing the guide arms in a disengaged position;

FIG. 4 is a sectional view taken along line 4—4 of FIG. 1;

FIG. 5 is an alternative embodiment of the sectional view taken along line 4—4 of FIG. 1;

BEST MODE OF CARRYING OUT INVENTION

Figure 1:
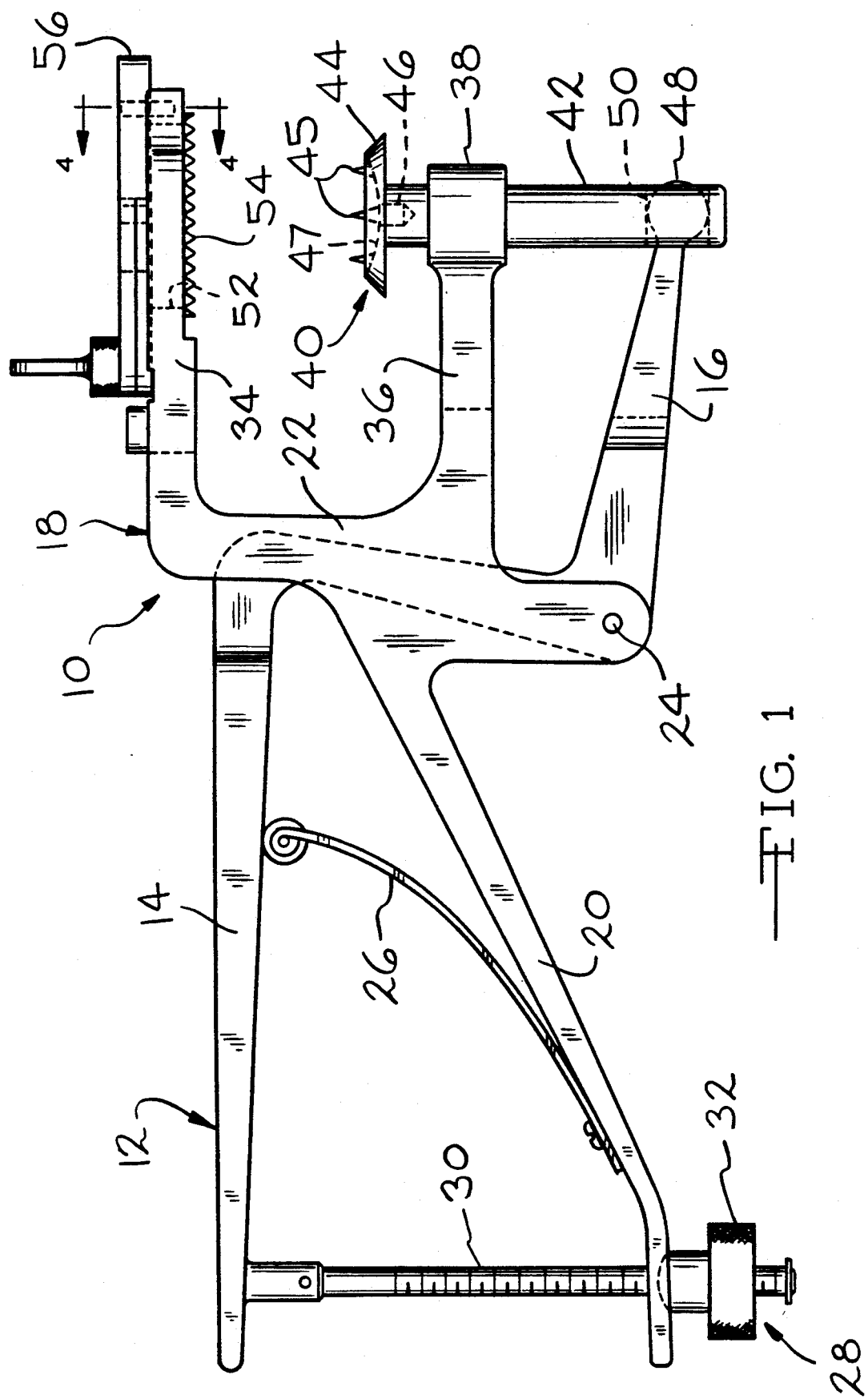
FIG. 1 is a side elevational view showing the universal patellar clamp of the present invention.

Referring now to FIGS. 1-5, there is shown a universal patellar clamp generally designated by numeral 10. The clamp 10 is preferably constructed of two distinct units; a generally Z-shaped member 12 forming an upper grip member 14 at one extreme and pivot arm 16 at the opposed extreme; and a second member 18 generally shown to form a lower grip member 20 at one extreme and a generally U-shaped clamping member 22 at the opposed extreme. The Z-shaped member 12 and the second member 18 are pivotally interconnected at pivot point 24. A resilient means 26 is positioned between the upper grip member 14 and lower grip member 20, acting to force the upper and lower grip members 14, 20 in an outwardly expansive resting position. It can be seen from viewing FIG. 1 that the farther the upper grip member 14 and the lower grip member 20 are separated, the farther the pivot arm 16 will be positioned away from the clamping member 22. A locking member 28 consisting of a bolt 30 and thumb nut 32 is engaged with the upper grip member 14 and lower grip member 20 to provide the specific desired limitations on the outward expansion of the grip members 14, 20 as caused by the resilient member 26.

The clamping member 22 of this invention is, preferably, shown to be of a generally U-shaped configuration defining an articular surface clamping member 34 integrally formed along one of the arms of the U. The opposed arm 36 of the U-shape extends parallel to the articular surface clamping member 34. The opposed arm 36 defines a centering member 38 which is positioned on the centerline axis of the articular surface clamping member 34. An anterior or subcutaneous clamping member 40 is engaged by the centering member 38. The anterior clamping member 40 includes a shaft 42 having a cup-shape unit 44 formed at the end closest in proximity to the articular surface clamping member 34. The end of the shaft 42 opposed to the cup-shape unit 44 is engaged with the pivot arm 16. The cup-shape unit 44 further includes a plurality of spike members 45 extending upwardly from the surface 47 of the cup-shape unit 44. The spike members 45 are preferably 2 to 4 mm in length.

Preferably, a hole or indent 46 is formed in the cup-shape unit 44 at the centerline axis of the articular surface clamping member 34. Preferably, the hole is 4 to 6 mm in diameter and 4 to 6 mm deep.

The engagement between the shaft 42 and the pivot arm 16 is achieved by means of a sliding pivot joint. The pivot joint consists of a ball member 48 formed on the end of the pivot arm 16. The ball member 48 is engaged in a retention slot 50 which allows the ball member 48 to slide in the retention slot 50 in a direction transverse to the movement of the shaft 42 along the centerline axis of the articular surface clamping member 34.

The articular surface clamping member 34 is generally donut shaped, defining a center aperture 52 having an inner diameter measuring 31-36 mm. The engagement surface 54 of the articular surface clamping member 34 is preferably serrated completely around the surface. In the preferred embodiment of this invention, the depth of the serration are 2 to 4 mm. Alternatively, the serration may only be partially located around the engagement surface 54 of the clamping member 34.

A pair of guide arms 56 are affixed to the neck 58 of the articular surface clamping member 34. The guide arms 56 are centered by engaging a stop member 62 and are retained in position by a locking nut 60. When the locking nut 60 is in a loosened configuration, the guide arms 56 are free to pivot about the locking nut 60 from a position engaged with the articular surface clamping member 34 as shown in FIG. 2 to a second position disengaged from the articular surface clamping member 34 as shown in FIG. 3. When the guide arms 56 are in an engaged position with the articular surface clamping member 34 as shown in FIG. 2, they cooperate to form a guidewire hole 64 which is positioned directly along the centerline axis of the center aperture 52 of the articular surface clamping member 34. The guide arms 56 are retained in their engaged position with the articular surface clamping member 34 by use of the locking nut 60 and a recessed slot 66 located in the upper surface of the clamping member 34 as shown in FIG. 4. Alternatively, as shown in FIG. 5, the guide arms 56 may be retained in position by a locking pin 68 which is inserted through the guide arms 56 into the clamping member 34, without benefit of the recessed slot 66.

Figure 6:
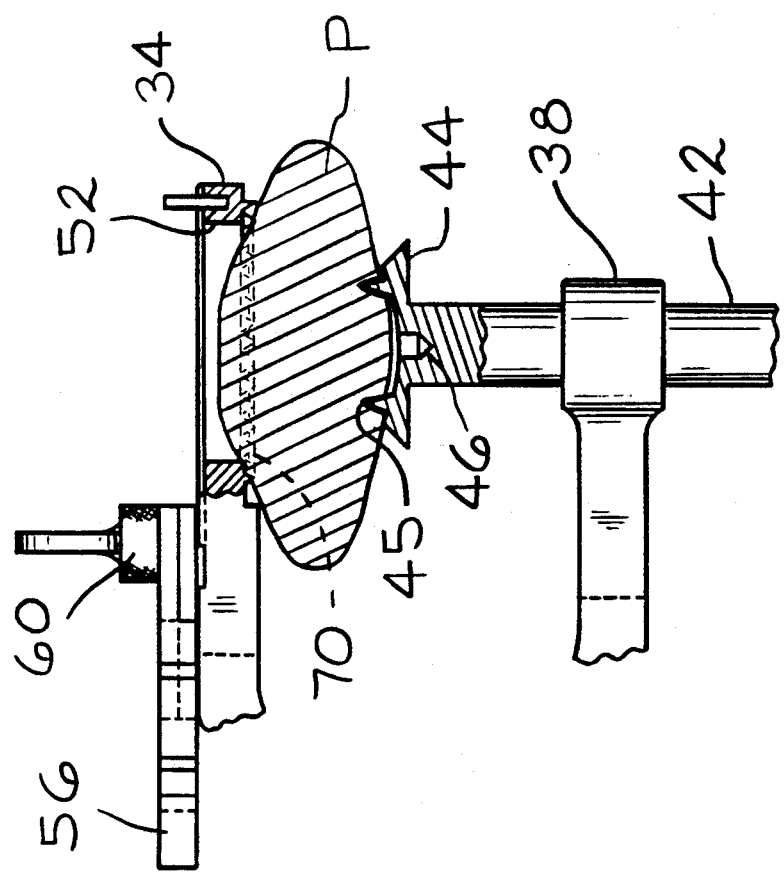
FIG. 6 is a sectional view of a patella initially engaged with the universal clamp of the present invention.

Referring now to FIG. 6, a human patella P is shown as it is engaged by the universal patellar clamp of this invention. After the top of the apex of the patella has been removed to form a substantially planar surface 70, the patellar clamp is aligned with the planar surface to effect the full engagement of the articular surface clamping member 34 with the planar surface 70. Upon achieving the proper positioning of the articular surface clamping member 34 the upper grip member 14 and lower grip member 20 are squeezed together to cause the pivot arm 16 to drive the anterior clamping member 40 into engagement with the subcutaneous tissue of the patella. The spike members 45 insert into the tissue to prevent slippage of the patella while clamped between the articular surface clamping member 34 and anterior clamping member 40. Once proper tension between the clamping members 34, 40 has been achieved, the thumb nut 32 of the locking member 28 is tightened to prevent the upper grip member 14 and lower grip member 20 from separating.

Figure 7:
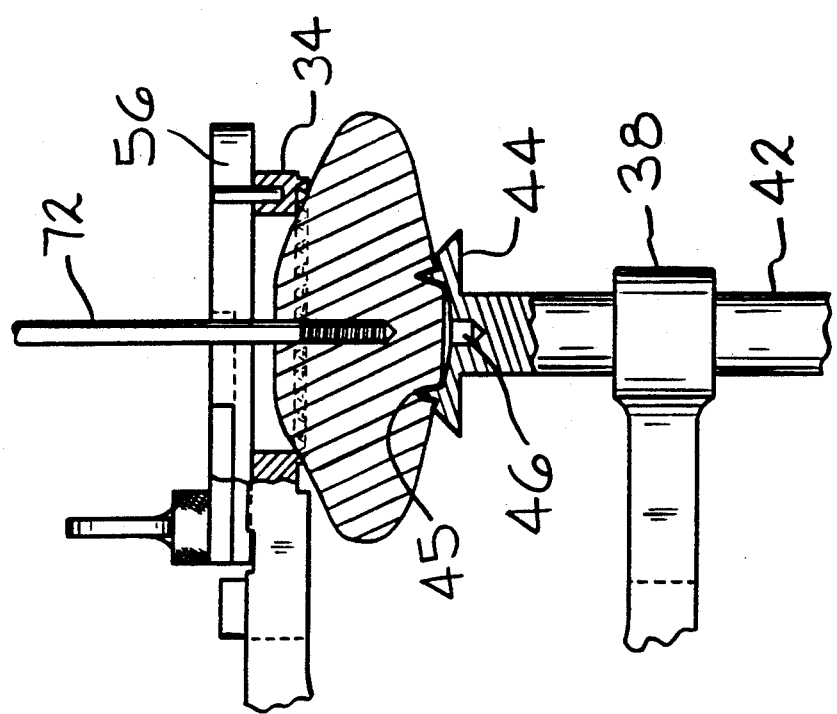
FIG. 7 is a sectional view of a patella during the initial step of drilling the guidewire into the patella using the guide arms to properly position the guidewire on the centerline axis.

Referring now to FIG. 7, the guide arms 56 are shown in their engaged position with the articular surface clamping member 34 and reaming with the combination guidewire and drill 72 has begun. The guidewire/drill 72 is reamed through the patella P and into the hole 46 where it is retained in aligned position with the centerline axis of the articular clamping member 34.

Figure 9:
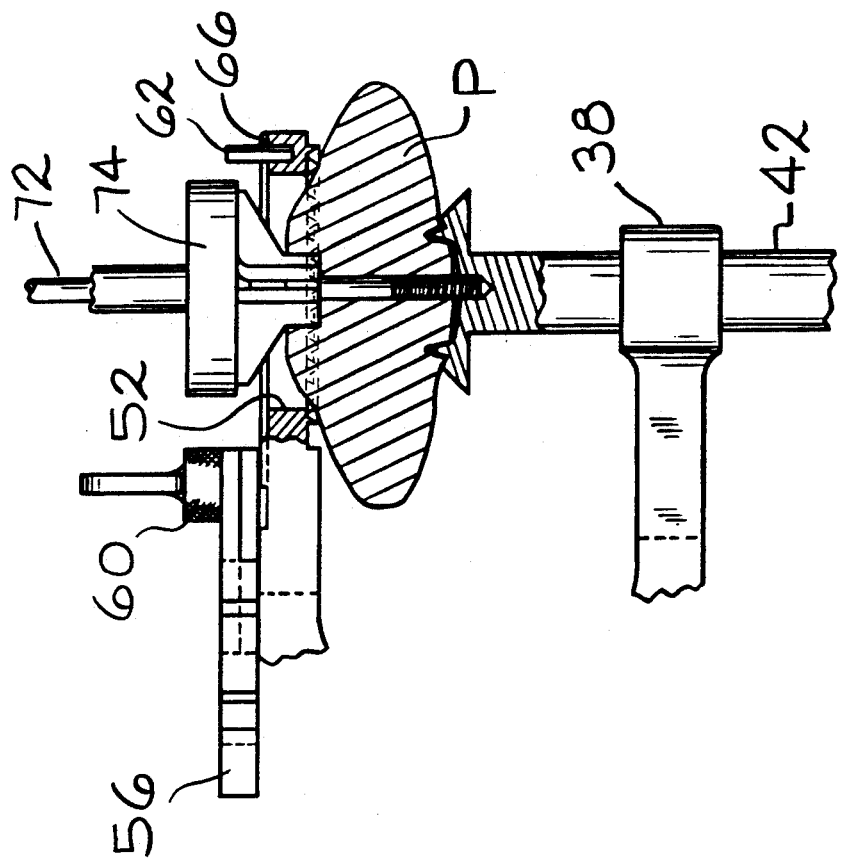
FIG. 9 is a sectional view of the patella with the guide arms disengaged and the cannulated reamer positioned for operation.
Figure 8:
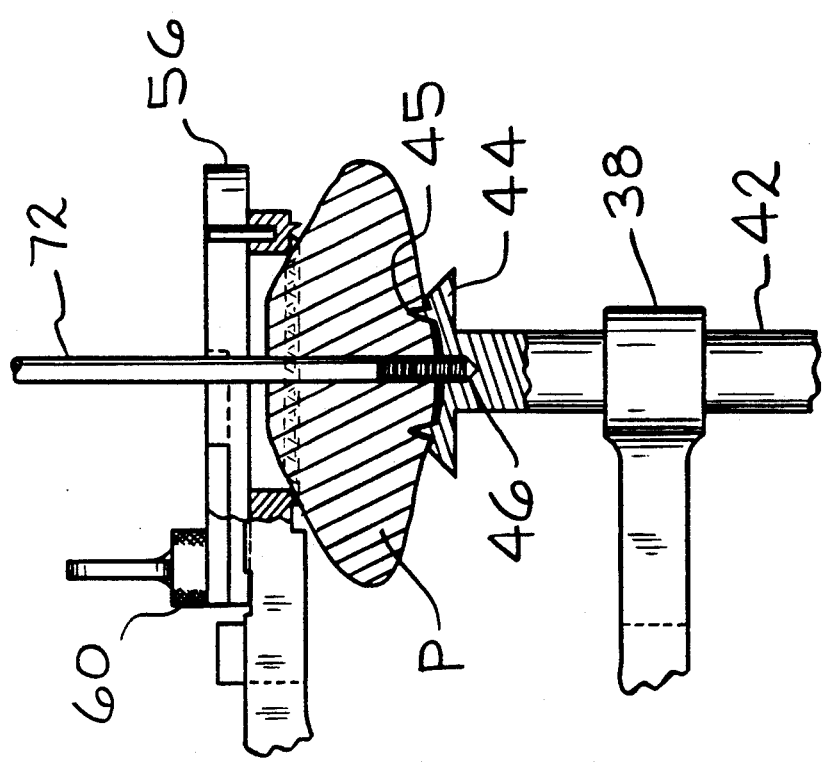
FIG. 8 is a sectional view of the patella with the guidewire in its final position.

Referring now to FIGS. 8 and 9, the guidewire/drill 72 is shown in its final position extending through the patella P into the hole 46 of the cup-shape unit 44. The guide arms 56 are then removed from engagement with the articular surface clamping member 34, thus opening access to the center aperture 52. A cannulated reamer 74 is positioned over the guidewire 72 and is placed in position within the center aperture 52 for properly reaming the patella.

Figure 11:
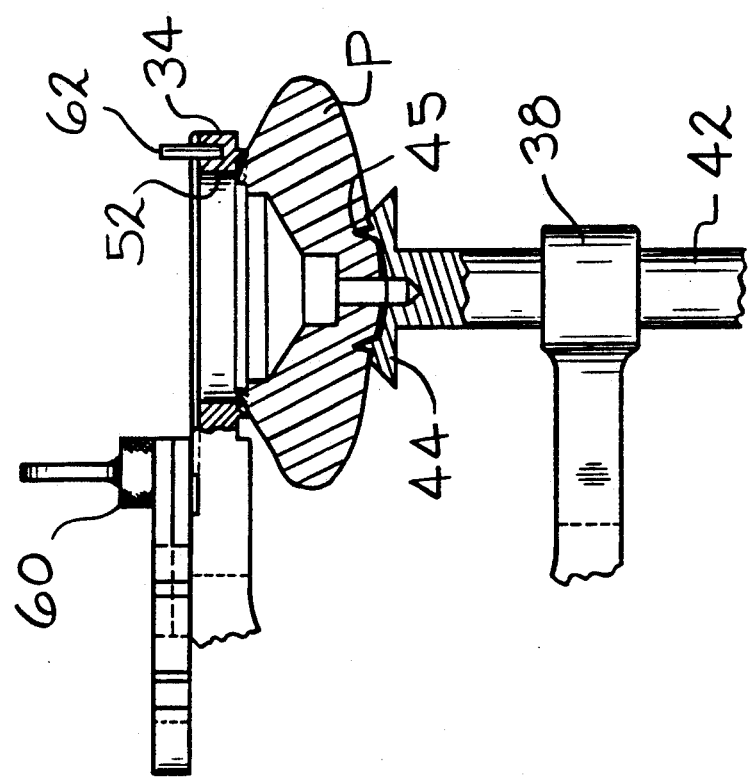
FIG. 11 is a sectional view of the patella having the work thereon completed and the cannulated reamer and guidewire removed.
Figure 10:
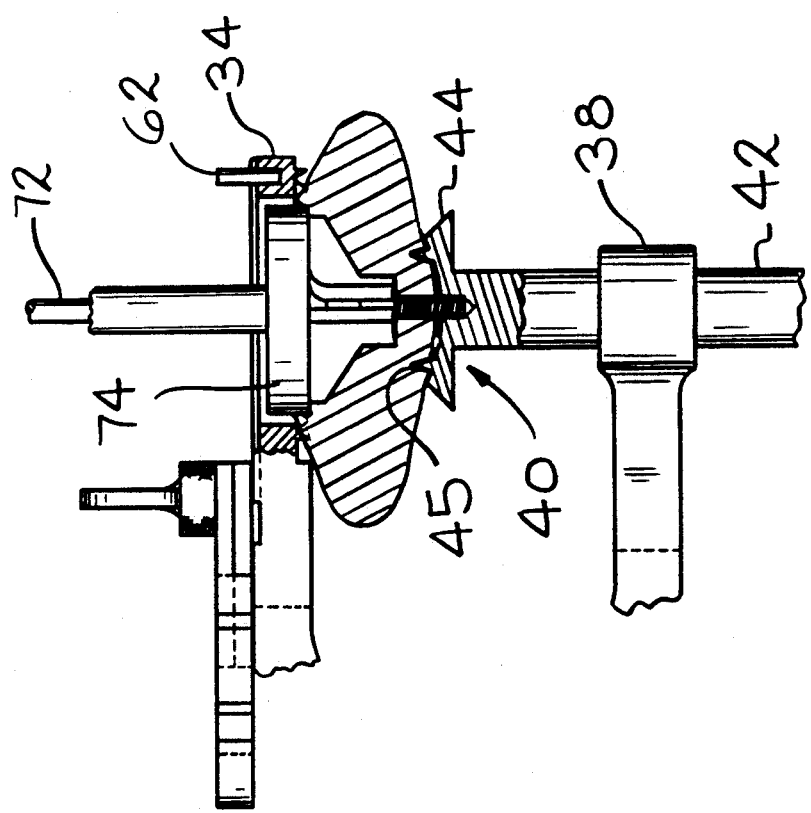
FIG. 10 is a sectional view of the patella showing the cannulated reamer having completed its reaming step.

Referring now to FIGS. 10 and 11, the reaming step is completed and the cannulated reamer 74 and guidewire 72 are shown in their final positions in the patella P. After the cannulated reamer 74 and guidewire 72 are removed, the patella P is left with the appropriate recess for receiving the patellar prosthesis.

Many modifications and embodiments will become readily apparent to those skilled in the art. Accordingly, the scope of the present invention should be determined only by the scope of the appended claims.

I claim:

1. A patellar clamp for use in the procedure of implanting a patellar prosthesis in a human patella comprising, in combination:
    an articular surface clamping member having a central aperture of a generally circular shape defining a centerline axis;
    an anterior surface clamping member positioned proximate said articular surface clamping member and adapted for movement along such centerline axis, said anterior surface clamping member including a patella engagement member supported by a shaft member, said patella engagement member including an aperture centered on such centerline axis;
    centering means for retaining said anterior surface clamping member oriented on such centerline axis;
    a first grip member fixed to said articular surface clamping member and second grip member engaged with said anterior surface clamping member, said first and second grip members being affixed together such that movement of said second grip member towards and away from said first grip member creates concomitant movement of said anterior surface clamping member towards and away from said articular surface clamping member; and,
    guide means positioned on said articular surface clamping member for providing centerline axis orientation for a reaming tool guidewire and drill used in such implanting procedure, said guide means being movable about such centerline axis orientation to expose said central aperture for access by a cannulated reamer.

2. The patellar clamp of claim 1, wherein said aperture is 4-6 mm in diameter and 4-6 mm deep.

3. A patellar clamp for use in the procedure of implanting a patellar prosthesis in a human patella comprising, in combination:
    an articular surface clamping member having a central aperture defining a centerline axis;
    an anterior surface clamping member positioned proximate said articular surface clamping member and adapted for movement along such centerline axis, said anterior surface clamping member including a patella engagement member supported by a shaft member;
    centering means including a centering member having a sleeve positioned about such centerline axis, said sleeve being adapted to engage said shaft and maintain said shaft in an oriented position on said centerline axis;
    a first grip member fixed to said articular surface clamping member and a second grip member engaged with said anterior surface clamping member, said first and second grip members being affixed together such that movement of said second grip member towards and away from said first grip member creates concomitant movement of said anterior surface clamping member towards and away from said articular surface clamping member; and,
    guide means positioned on said articular surface clamping member for providing centerline axis orientation to reaming tools used in such implanting procedure, said guide means being removable from such centerline axis orientation to expose said central aperture.

4. The patellar clamp of claim 3, wherein said centering member is integrally fixed to said anterior clamping member.

5. A patellar clamp for use in the procedure of implanting a patellar prosthesis in a human patella comprising, in combination:
    an articular surface clamping member having a central aperture defining a centerline axis;
    an anterior surface clamping member positioned proximate said articular surface clamping member and adapted for movement along such centerline axis;
    centering means for retaining said anterior surface clamping member centered on such centerline axis;
    a first grip member fixed to said articular surface clamping member and a second grip member engaged with said anterior surface clamping member, said first and second grip members being affixed together such that movement of said second grip member towards and away from said first grip member creates concomitant movement of said anterior surface clamping member towards and away from said articular surface clamping member; and, guide means positioned on said articular surface clamping member for providing centerline axis orientation to reaming tools used in such implanting procedure, said guide means including first and second guide arms pivotally engaged with said articular surface clamping member, wherein said guide arms rotate into a first position engaged over said central aperture to define a guide hole at such centerline axis and a second position disengaged from and clearing said central aperture.

6. The patellar clamp of claim 5, wherein said guide arms are retained in their first position over said central aperture by engagement with a recessed slot formed in said articular surface clamping member.

7. The patellar clamp of claim 5, wherein said guide arms are retained in their first position over said central aperture by a locking pin inserted through said guide arms and fixed to said articular surface clamping member.

8. The patellar clamp of claim 5, further including a guide arm locking member at such point of pivotal engagement for locking said first and second guide arms into any position relative to each other and said central aperture.

9. A patellar clamp for use in the procedure of implanting a patellar prosthesis in a human patella comprising, in combination:

an articular surface clamping member having a central aperture defining a centerline axis;

an anterior surface clamping member positioned proximate said articular surface clamping member and adapted for movement along such centerline axis;

means for moving at least one of said articular surface clamping member and said anterior surface clamping member towards and away from the other;

guide means engaged with said articular surface clamping member for providing centerline axis orientation to reaming tools used in such implanting procedure, said guide means including first and second guide arms pivotally engaged with said articular surface clamping member, wherein said guide arms rotate into a first position engaged over said central aperture to define a guide hole at such centerline axis and a second position disengaged from and clearing said central aperture.

10. The patellar clamp of claim 9, wherein said guide arms are retained in their first position over said central aperture by engagement with a recessed slot formed in said articular surface clamping member.

11. The patellar clamp of claim 9, wherein said guide arms are retained in their first position over said central aperture by a locking pin inserted through said guide arms and fixed to said articular surface clamping member.

12. The patellar clamp of claim 9, further including a guide arm locking member at such point of pivotal engagement for locking said first and second guide arms into any position relative to each other and said central aperture.

13. A patellar clamp for use in the procedure of implanting a patellar prosthesis in a human patella comprising, in combination:

an articular surface clamping member having a central aperture defining a centerline axis;

an anterior surface clamping member positioned proximate said articular surface clamping member and adapted for movement along such centerline axis, said anterior surface clamping member including a patella engagement member supported by a shaft member;

centering means for retaining said anterior surface clamping member centered on such centerline axis;

a first grip member fixed to said articular surface clamping member and a second grip member engaged with said anterior surface clamping member, said second grip member including a pivot arm engaged to said shaft member, said pivot arm defining a ball member and said shaft member defining a retention slot for engaging said ball member wherein said ball member is free to move in a direction transverse to said centerline axis within said retention slot as said pivot arm moves said anterior surface clamping member along such centerline axis, said first and second grip members being fixed together such that movement of said second grip member towards and away from said first grip member creates concomitant movement of said anterior surface clamping member towards and away from said articular surface member; and, guide means positioned on said articular surface clamping member for providing centerline axis orientation to reaming tools used is such implanting procedure, said guide means being removable from such centerline axis orientation to expose said central aperture.

* * * * *